(12) United States Patent
Hunt

(10) Patent No.: US 8,475,512 B2
(45) Date of Patent: Jul. 2, 2013

(54) PROSTHETIC VALVE DEVICES AND METHODS OF MAKING AND USING SUCH DEVICES

(75) Inventor: James B. Hunt, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 693 days.

(21) Appl. No.: 11/435,057

(22) Filed: May 16, 2006

(65) Prior Publication Data
US 2006/0265053 A1 Nov. 23, 2006

Related U.S. Application Data

(60) Provisional application No. 60/681,838, filed on May 17, 2005.

(51) Int. Cl.
*A61F 2/06* (2006.01)

(52) U.S. Cl.
USPC .......................................... 623/1.1; 623/1.24

(58) Field of Classification Search
USPC .............. 623/1.24, 2.12, 1.21, 1.32, 2.23, 623/2.1
See application file for complete search history.

(56) References Cited

U.S. PATENT DOCUMENTS

| | | | |
|---|---|---|---|
| 4,675,361 A | 6/1987 | Ward et al. | |
| 4,861,830 A | 8/1989 | Ward et al. | |
| 4,902,508 A | 2/1990 | Badylak et al. | |
| 5,017,664 A | 5/1991 | Grasel et al. | |
| 5,314,473 A | 5/1994 | Godin | |
| 5,554,389 A | 9/1996 | Badylak et al. | |
| 5,589,563 A | 12/1996 | Ward et al. | |
| 5,690,642 A | 11/1997 | Osborne et al. | |
| 5,713,950 A | 2/1998 | Cox | |
| 5,814,061 A | 9/1998 | Osborne et al. | |
| 5,824,063 A | 10/1998 | Cox | |
| 5,855,597 A | 1/1999 | Jayaraman | |
| 5,993,844 A | 11/1999 | Abraham et al. | |
| 6,099,567 A | 8/2000 | Badylak et al. | |
| 6,126,686 A | 10/2000 | Badylak et al. | |
| 6,206,931 B1 | 3/2001 | Cook et al. | |
| 6,338,740 B1 * | 1/2002 | Carpentier | 623/2.13 |
| 6,358,277 B1 * | 3/2002 | Duran | 623/2.12 |
| 6,371,961 B1 | 4/2002 | Osborne et al. | |
| 6,596,024 B2 * | 7/2003 | Chinn | 623/2.17 |
| 6,602,286 B1 * | 8/2003 | Strecker | 623/1.24 |
| 6,716,241 B2 | 4/2004 | Wilder et al. | |
| 6,726,715 B2 * | 4/2004 | Sutherland | 623/2.1 |
| 6,752,826 B2 | 6/2004 | Holloway et al. | |

(Continued)

FOREIGN PATENT DOCUMENTS

| | | |
|---|---|---|
| WO | WO 03/002165 A1 | 1/2003 |
| WO | WO 2004/080352 A1 | 9/2004 |
| WO | WO 2004/082528 A2 | 9/2004 |
| WO | WO 2004/089253 A1 | 10/2004 |

OTHER PUBLICATIONS

PCT Search Report for PCT/US2006/019184.

*Primary Examiner* — David H Willse
*Assistant Examiner* — Tiffany Shipmon
(74) *Attorney, Agent, or Firm* — Buchanan Nipper

(57) ABSTRACT

The present invention relates to medical devices and in particular to frameless grafting prostheses and methods of making and using such devices. The frameless grafting prostheses include a stiffening member useful in the attachment of the frameless grafting prostheses to a wall of a body lumen.

20 Claims, 6 Drawing Sheets

U.S. PATENT DOCUMENTS

| | | |
|---|---|---|
| 6,752,828 B2 | 6/2004 | Thornton |
| 6,939,377 B2 | 9/2005 | Jayaraman et al. |
| 6,946,539 B2 * | 9/2005 | Sunkara .................... 528/76 |
| 2001/0039450 A1 | 11/2001 | Pavcnik et al. |
| 2002/0045936 A1 * | 4/2002 | Moe ........................ 623/2.17 |
| 2002/0187288 A1 | 12/2002 | Lin et al. |
| 2003/0014126 A1 | 1/2003 | Patel et al. |
| 2003/0130726 A1 | 7/2003 | Thorpe et al. |
| 2003/0149471 A1 | 8/2003 | Briana et al. |
| 2003/0191525 A1 | 10/2003 | Thornton |
| 2004/0034409 A1 | 2/2004 | Heublein et al. |
| 2004/0073297 A1 | 4/2004 | Rohde et al. |
| 2004/0186558 A1 | 9/2004 | Pavcnik et al. |
| 2004/0210303 A1 * | 10/2004 | Sedransk ................... 623/2.1 |
| 2004/0230297 A1 * | 11/2004 | Thornton .................. 623/1.24 |
| 2004/0243222 A1 * | 12/2004 | Osborne et al. ........... 623/1.24 |
| 2006/0167542 A1 * | 7/2006 | Quintessenza ............ 623/2.12 |
| 2006/0210597 A1 * | 9/2006 | Hiles ........................ 424/422 |
| 2006/0212110 A1 | 9/2006 | Osborne et al. |
| 2006/0235511 A1 * | 10/2006 | Osborne .................... 623/2.12 |
| 2007/0027535 A1 * | 2/2007 | Purdy et al. ............... 623/2.18 |
| 2007/0043431 A1 * | 2/2007 | Melsheimer ............... 623/1.24 |
| 2007/0043435 A1 * | 2/2007 | Seguin et al. .............. 623/2.11 |
| 2007/0080188 A1 * | 4/2007 | Spence et al. ............. 227/175.1 |

* cited by examiner

PROSTHETIC VALVE DEVICES AND METHODS OF MAKING AND USING SUCH DEVICES

RELATED APPLICATIONS

This non-provisional patent application claims priority to U.S. Provisional Patent Application No. 60/681,838, filed May 17, 2005, the contents of which are incorporated by reference in their entirety.

FIELD OF THE INVENTION

The present invention relates to medical devices and in particular to prosthetic valve devices and methods of making and using such devices.

BACKGROUND OF THE INVENTION

Many vessels in animals transport fluids from one bodily location to another. In some vessels, natural valves are positioned along the length of the vessel to permit fluid flow in a substantially unidirectional manner along the length of the vessel.

For example, by use of a closed circulatory system, animal bodies use many internal organs and vessels to transport fluids from one bodily location to another. Components of the circulatory system include the heart, blood vessels, and blood. The heart has valves that regulate the flow of blood in the atria and the ventricles. Three examples of blood vessels are arteries, veins, and capillaries. Whereas arteries transport blood to organs throughout the body (i.e., away from the heart), veins carry blood back to the heart. Structurally, capillaries have an inner endothelium surrounded by a membrane, while arterial and venal walls have three layers: connective tissue forms the outer layer, while smooth muscle having elastic fibers forms the middle layer, and there is an innermost endothelium layer.

Mammalian veins have naturally occurring valves positioned along the length of the vessel. These valves act as one-way check valves that open to permit the flow of fluid in a first direction (e.g., muscles contract, squeeze the veins, and the valves—flaps of tissue—keep blood moving toward the heart (antegrade flow)), and quickly close upon a change in pressure, such as a transition from systole to diastole, or when muscles relax or stop contraction, to prevent fluid flow in a reverse direction, i.e., retrograde flow.

Natural valves may have a leakiness quality to them, allowing a relatively small quantity of fluid to flow in a reverse direction (i.e., a second direction opposed to the first direction; retrograde flow) when the valve is in closed position. It is believed that this leakiness limits the pooling of blood around the valve during periods of low pressure, which can reduce the formation of thrombus and, therefore, increase the effective lifetime of the valve.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency may be present and can lead to discomfort and possibly ulcers in the legs and ankles.

Current treatments for venous valve insufficiency include the use of compression stockings that are placed around the leg of a patient in an effort to force the vessel walls radially inward to restore valve function. Surgical techniques are also employed in which valves can be bypassed or replaced with sections of veins with competent valves.

Over recent years, a wide variety of minimally invasive techniques and instruments for placement of intraluminal medical devices have been developed. Such treatment devices include stents, stent grafts, occlusion devices, infusion catheters and the like. Minimally invasive intravascular devices have especially become popular with the introduction of coronary stents to the U.S. market in the early 1990s. Coronary and peripheral stents have been proven to provide a superior means of maintaining vessel patency, and have become widely accepted in the medical community. Furthermore, the use of stents has been extended to treat aneurysms and to provide occlusion devices, among other uses.

Artificial valves have been proposed to replace damaged natural valves. One variety of such artificial valves consists of a stent supporting one or more valve leaflets. The leaflets are configured to allow flow in an antegrade direction and to restrict flow in a retrograde direction. One drawback to this type of valve is that the supporting stent contacts the wall of the vessel in the region of placement of the valve. This can result in irritation of the vessel wall, resulting in intimal hyperplasia and thrombosis.

In another variety of artificial valve, the valve leaflet is attached to and supported by the vessel wall. Such artificial valves do not include a support stent and offer the advantage of reduced irritation of the vessel wall in the region of attachment of the valve. However, the absence of a supporting stent can result in difficulties during the delivery of the valve to the site of attachment to the vessel wall and during the process of attachment of the valve leaflet to the wall.

SUMMARY

In one embodiment, the invention provides a frameless grafting prosthesis for implantation in a body lumen having a lumen wall. The frameless grafting prosthesis includes at least one shaped valve cusp having a top edge, a base edge, side edges extending from the base edge to the top edge, an anchoring element attached to the base edge, and a stiffening member positioned within the valve body so as to allow a force sufficient to attach the anchoring element to the lumen wall to be transmitted from a pushing surface on the top edge to the anchoring element. The anchoring element is configured to attach to or penetrate a wall of the body lumen and can be, for example, a barb or a hook. The anchoring element can also be a surface having an adhesive attached.

In one embodiment, the stiffening member extends from the base edge and terminates at the pushing surface on the top edge.

In another embodiment, the shape of the pushing surface is adapted to receive an end of a push rod. In another embodiment, the pushing surface includes a biocompatible adhesive. In yet another embodiment, the pushing surface includes a magnetic or magnetically responsive element.

The stiffening member can include a material selected from a group consisting of stainless steel, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, a fluoroplastic, such as polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

In another aspect, the invention provides a system for delivery and attachment of the frameless grafting prosthesis to the wall of a body lumen. The system includes a frameless grafting prosthesis, such as that described herein, and a deployment device for the frameless grafting prosthesis. The deployment device includes a central portion, a retractable sheath surrounding the central portion and defining an enclosure between the central portion and the retractable sheath, and a push rod having an end surface. The shaped valve cusp is positioned within the enclosure such that a push rod extends through the deployment device so that a portion of the end surface is adjacent to or in contact with the pushing surface.

In another aspect, the invention provides a method for delivering and attaching the frameless grafting prosthesis to the wall of a body lumen. The method includes positioning the deployment system at a required position within the body lumen, and applying a force to the pushing surface of the shaped valve cusp with the push rod. The force is transmitted to the anchoring element by the stiffening member and is sufficient to push the frameless grafting prosthesis out of the enclosure and to push the anchoring element against, into or through the wall of the body lumen.

These and other aspects, advantages, and features of the invention will become apparent from the following figures and detailed description of the embodiments.

DEFINITIONS

Figure 1A:
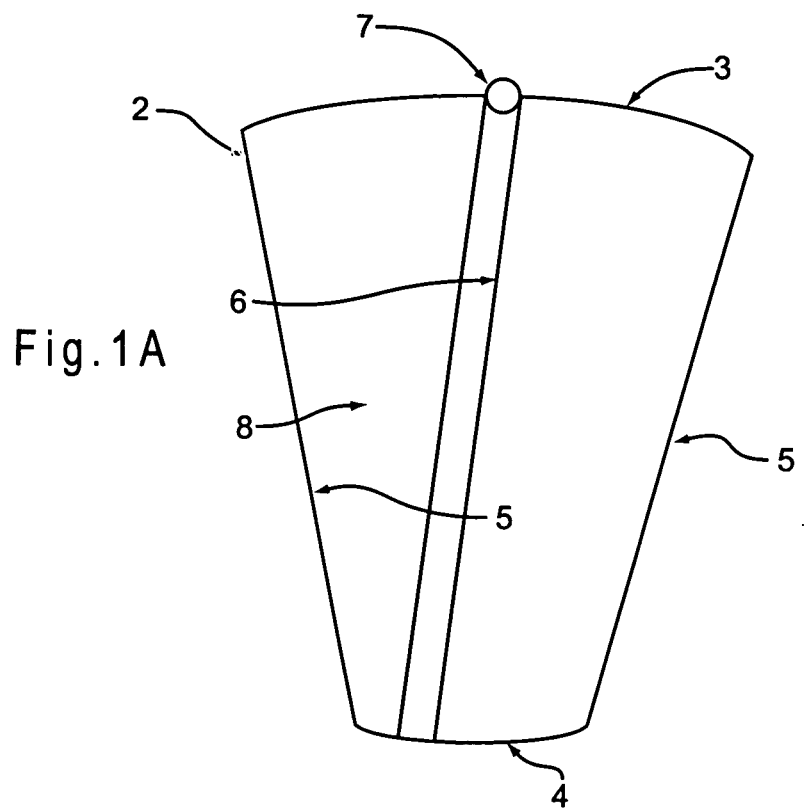
FIG. 1(a) provides a perspective view of a frameless grafting prosthesis having one shaped valve cusp containing a stiffening member.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The term "implantable" refers to an ability of a medical device to be positioned at a location within a body, such as within a body vessel. Furthermore, the terms "implantation" and "implanted" refer to the positioning of a medical device at a location within a body, such as within a body vessel.

An "alloy" is a substance composed of two or more metals or of a metal and a nonmetal united, such as by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

A "biodegradable" material is a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

A "biocompatible" material is a material that is compatible with living tissue or a living system by not being toxic or injurious and not causing immunological rejection.

A "non-bioabsorbable" or "biostable" material refers to a material, such as a polymer or copolymer, which remains in the body without substantial dissipation.

A "remodelable material" is a material that, when implanted in vivo, is capable of being resorbed by the body or providing a matrix for the regrowth of autologous cells. In some embodiments, fluid contacting autologous cells on an implanted remodelable material interface can affect the growth of autologous tissue on the implanted remodelable material.

The phrase "controlled release" refers to the release of an agent at a predetermined rate. A controlled release may be constant or vary with time. A controlled release may be characterized by a drug elution profile, which shows the measured rate that the agent is removed from a device in a given solvent environment as a function of time. For example, a controlled release elution profile from a valve prosthesis may include an initial burst release associated with the deployment of the valve prosthesis, followed by a more gradual subsequent release. A controlled release may be a gradient release in which the concentration of the agent released varies over time or a steady state release in which the agent is released in equal amounts over a certain period of time (with or without an initial burst release).

As used herein, the phrase "bioactive agent" refers to any pharmaceutically active agent that produces an intended therapeutic effect on the body to treat or prevent conditions or diseases.

DESCRIPTION OF THE ILLUSTRATIVE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Devices and systems of the invention are desirably adapted for deployment within a body lumen, and in particular embodiments, devices and systems of the invention are adapted for deployment within the venous system. Accordingly, preferred devices adapted are venous valves, for example, for percutaneous implantation within veins of the legs or feet to treat venous insufficiency. However, devices and systems of the present invention may be adapted for deployment within any tube-shaped body passage lumen that conducts fluid, including but not limited to blood vessels such as those of the human vasculature system, billiary ducts and ureteral passages.

The present invention provides frameless grafting prosthesis devices, and systems and methods for the delivery thereof. With reference now to FIG. 1(a), shown is an illustrative frameless grafting prosthesis of the present invention. The illustrated embodiment of the frameless grafting prosthesis includes a one shaped valve cusp 2 having a stiffening member 6.

The shaped valve cusp 2 includes a flexible valve body 8 defined by a top edge 3, a base edge 4, and side edges 5 extending from the base edge to the top edge. A stiffening member 6 extends from the base edge 4 to a pushing surface 7 on the top edge 3. Stiffening member 6 is less flexible than the valve body 8 and is sufficiently rigid to permit a force applied to the pushing surface 7 to be transmitted to the base edge 4. The valve body 8 of shaped valve cusp 2 is sufficiently flexible to be deformable around an axis generally parallel to the stiffening member 6.

Figure 1B:
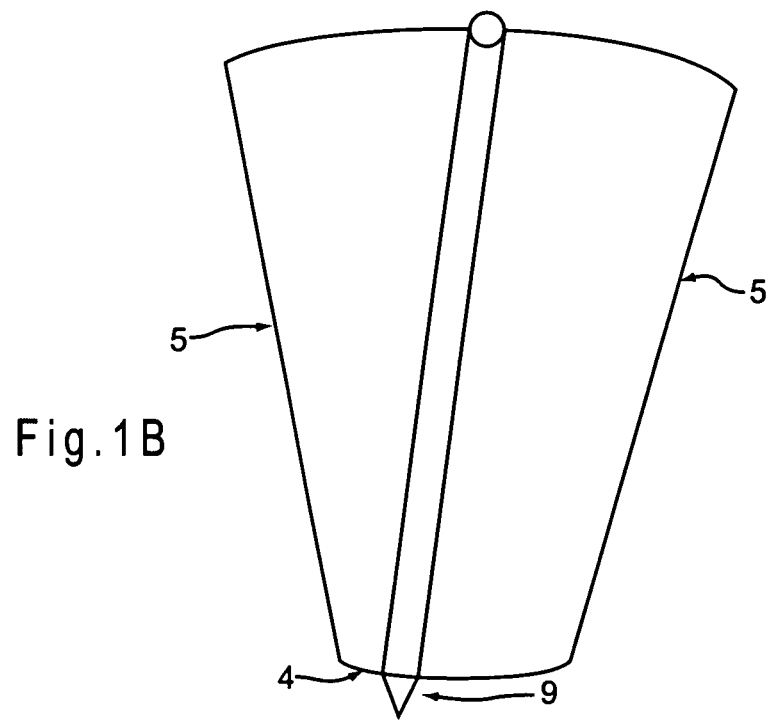
FIG. 1(b) provides a perspective view a frameless grafting prosthesis having one shaped valve cusp containing a stiffening member and an anchoring element.

With reference now to FIG. 1 (b), the shaped valve cusp can further include an anchoring element 9 attached to the base edge 4. The anchoring element 9 is configured to attach to or to partially or fully penetrate the wall of a body lumen. Additional anchoring elements can also be attached to the base edge 4, and to the side edges 5. The stiffening member 6 is positioned and is sufficiently rigid to allow a force sufficient to push anchoring element 9 against, into or through a lumen wall, to attach the frameless grafting prosthesis to the lumen wall, to be transmitted from pushing surface 7 to anchoring element 9. In the illustrated embodiment, a first end of the stiffening member 6 is directly contacting the anchoring element 9.

Figure 2A:
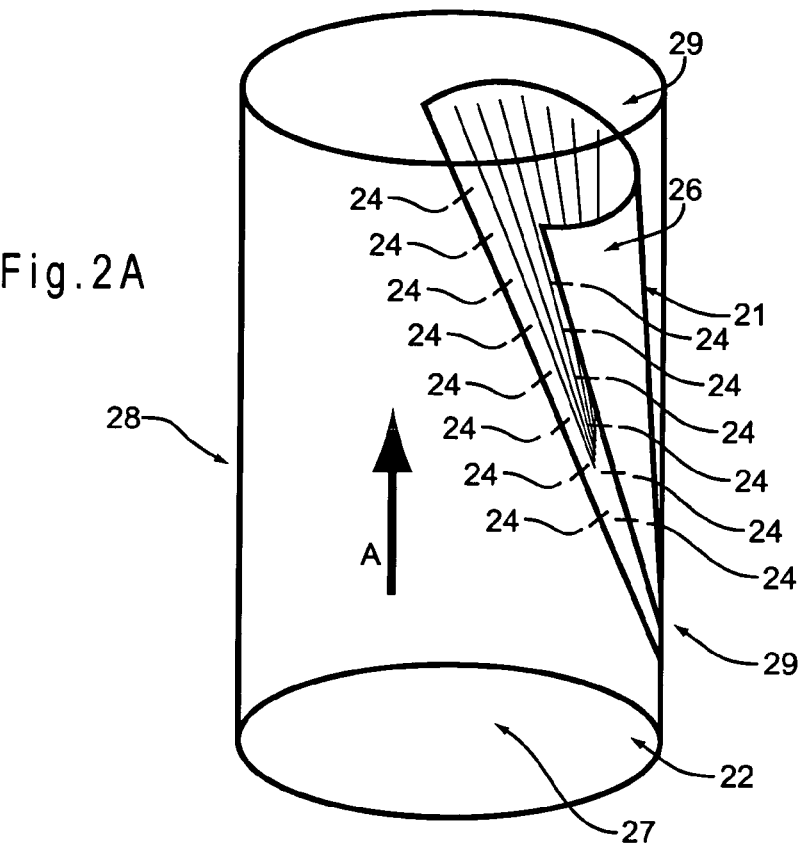
FIG. 2(a) provides a perspective view of a frameless grafting prosthesis having one shaped valve cusp placed in a body lumen. The shaped valve cusp is positioned to allow antegrade flow.
Figure 2B:
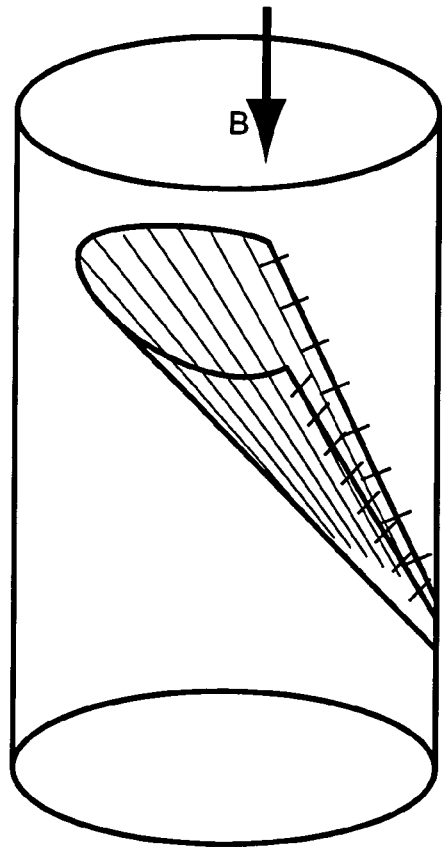
FIG. 2(b) provides a perspective view of a frameless grafting prosthesis having one shaped valve cusp placed in a body lumen. The shaped valve cusp is positioned to restrict retrograde flow.

FIGS. 2(a) and 2(b) illustrate a frameless grafting prosthesis 21 positioned in a body lumen 27 defined by a lumen wall 28. The shaped valve cusp is attached to lumen wall 28 via anchoring element 29. Additional means of attachment can also be present. For example, the base edge and side edges can be attached to the lumen wall 28 by further anchoring elements 24. Examples of anchoring elements, including barbs, hooks, and adhesives are described in International Patent Application serial number PCT/US2004/009971, filed Apr. 1, 2004, and published Oct. 21, 2004 as W004089253, the contents of which are incorporated by this reference.

The shaped valve cusp of frameless grafting prosthesis 21 is configured to facilitate the valve function by selectively allowing blood flow in a first direction (antegrade flow), and selectively restricting blood flow in a second direction opposite the first direction (retrograde flow). Frameless grafting prosthesis 21 in particular is designed to facilitate net blood flow (antegrade flow) in the direction of arrow A in FIG. 2(a). Shaped valve cusp 26 is formed with a flexible material and moves outwardly to a first position to open the lumen 27 when subjected to blood flow in the direction of arrow A. In this position, as is shown in FIG. 2(a), the body of the shaped valve cusp 26 is positioned close to the lumen wall so as to maximize the size of the opening in the lumen 27 and leave only a small pocket 29 between the shaped valve cusp 26 and the lumen wall 28.

As is illustrated in FIG. 2(b), the shaped valve cusp 26 moves inwardly to a second position to close the opening 27 when subjected to flow in the direction of arrow B (retrograde flow). The presence of stiffening member 6 does not prevent shaped valve cusp 26 from inverting from an open configuration (first position) when subject to antegrade flow to a closed configuration (second position) when subject to retrograde flow, and from reversing this configuration change upon reversal of the flow direction. As is explained below, stiffening member 6 allows for the attachment of shaped valve cusp 26 to the lumen wall 28 by permitting a force applied to a pushing surface 7 to be transmitted to anchoring element 9 so that anchoring element 9 is pushed towards the lumen wall 28 and attaches to or partially or fully penetrates the lumen wall 28.

Figure 3:
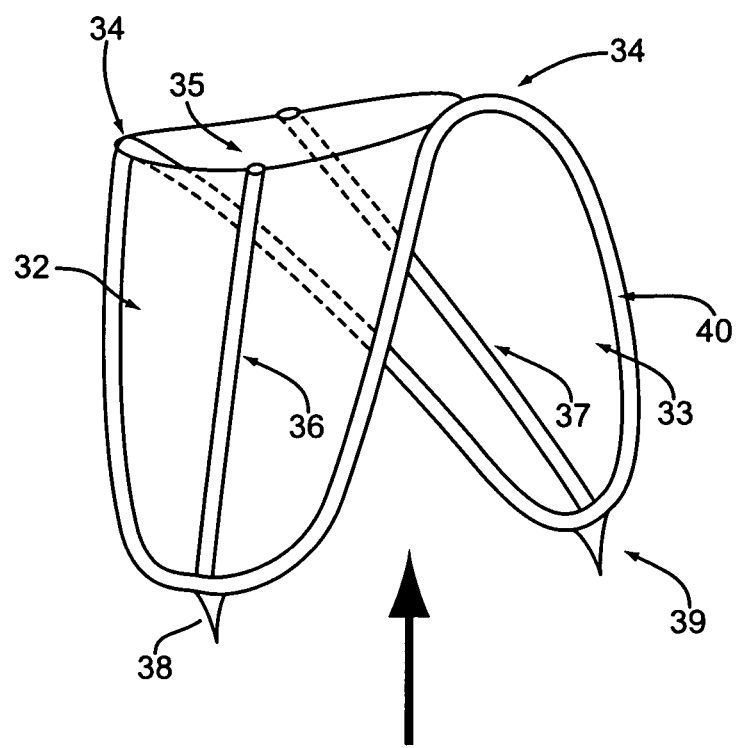
FIG. 3 provides a perspective view of a frameless grafting prosthesis having two shaped valve cusps.

With reference now to FIG. 3, shown is another illustrative frameless grafting prosthesis of the present invention. The illustrated embodiment of the frameless grafting prosthesis includes two shaped valve cusps 32 and 33 joined at the top of their side edges 34 to form an opening 35.

Opening 35 is configured to facilitate the valve function by selectively allowing blood flow in a first direction (antegrade flow), and selectively restricting blood flow in a second direction opposite the first direction (retrograde flow). Shaped valve cusps 32 and 33 include stiffening members 36 and 37 respectively. These members felicitate attachment of the frameless grafting prosthesis to a lumen wall by anchoring elements 38 and 39. As is the case of the single valve cusp, stiffening members 36 and 37 do not prevent shaped valve cusps 32 and 33 from inverting from an open configuration when subject to antegrade flow to a closed configuration when subject to retrograde flow.

The frameless grafting prosthesis can also include a lip 40 or other reinforcement along the edges of the shaped valve cusps 32 and 33. The lip 40 may be made from the same material or a different material than that of the valve cusps 32 and 33. For example, lip 40 may be made by folding, rolling, or otherwise gathering and securing material at the periphery of material from which valve cusps 32 and 33 are made. Alternatively, a different material may be secured to the periphery of valve cusps 32 and 33 to provide the lip or other reinforcement. Still further, valve cusps 32 and 33 may be integrally made with a reinforced lip 40, for example by molding, and/or material at the periphery of valve cusps 32 and 33 may be treated to increase its strength relative to the remainder of valve cusps 32 and 33, for example by adding crosslinking to the periphery where valve cusps 32 and 33 are made of collagenous materials. Reinforced lip 40 can include anchoring elements, for example, barbs, hooks, or adhesives.

It will be understood that other valve body configurations are contemplated as being within the scope of the present invention. For example, valves disclosed in published U.S. Publication Number. 20010039450A1, published Nov. 8, 2001, the contents of which are incorporated by reference, can be modified to provide valve devices and systems in accordance with the present invention (including the removal of any stent or frame elements present in the prior-disclosed valves). It will be understood in this regard that a frameless grafting prosthesis having one shaped valve cusp (monocuspid valve), or a plurality of shaped valve cusps, e.g. two (bicuspid valve), three (tricuspid valve), four (quadracuspid valve), or more shaped valve cusps, are contemplated as within the scope of the present invention. In the case of multicuspid valves, the shaped valve cusps may be of the same or differing dimensions.

When a monocusp leaflet configuration is utilized in the invention, the frameless grafting prosthesis having such a configuration can be dimensioned and attached in such a manner so as to allow the valve cusp to extend across the entire lumen and co-apt with the opposite wall. Alternatively, two or more monocusp devices can be provided and dimensioned for separate attachment to the wall so as to co-apt with each other within the lumen; for example, near the middle of the lumen.

When a multicusp leaflet configuration is utilized, the frameless grafting prosthesis will comprise at least two valve cusps, wherein the at least two valve cusps are attached to the wall in such a manner so as to allow the valve cusps to co-apt within the lumen, for example, near the center of the lumen.

Whatever configuration is utilized, it will be understood that antegrade flow will pass through the co-apt line i.e., the point where the monocusp valve co-apts with the opposite wall or where the at least two valve cusps co-apt within the lumen of the vein. On the other hand, retrograde flow will be restricted.

The frameless grafting prosthesis of the invention can be adapted to provide a shaped valve cusp having any suitable configuration. For example, the shaped valve cusp after implantation can have a non-planar configuration when in a closed condition. Preferably, the shaped valve cusp will have a generally concave/convex configuration when in a closed condition, as shown for example in FIGS. 2(*a*) and 2(*b*). Other configurations are contemplated, and can be designed through routine experimentation so as to allow for optimal flow through the valve.

The frameless grafting prosthesis of the invention can be constructed so as to have predetermined dimensions at its base, top edge, and sides, such that the prosthesis is adapted to provide a valve function in a vein or other vessel of a specific diameter. For example, the dimensions of the prosthesis can be selected so as to render the device suitable for providing a valve function in a vein or other vessel having an inner diameter of about 5 mm to about 50 mm, more typically in the range of about 8 mm to about 20 mm. Typically, for a valve having one cusp, the dimension of the top edge of the frameless grafting prosthesisis is approximately 50 percent of the inner circumference of the vessel. The dimension of the side edge is typically 50% to 500% that of the top edge.

In one embodiment, the side edges diverge from the base edge towards the top edge so that the valve cusp forms a segment of a cone. Such an embodiment is shown in FIG. 1. In another embodiment, the side edges and base edge are shaped to form a smooth transition at their meeting point.

Composition of the Frameless Grafting Prosthesis

The flexible material used in bodies of the shaped valve cusps is a biocompatible material, or is encased in a biocompatible material, and is, in one embodiment, a remodelable material. Suitable remodelable materials may be made from natural or synthetic polymers, including collagen. Thus, in general, the flexible material may comprise a synthetic biocompatible polymer such as cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material such as polytetrafluoroethylene, or mixtures or copolymers thereof; polylactic acid, polyglycolic acid or copolymers thereof, a polyanhydride, polycaprolactone, polyhydroxy-butyrate valerate, polyhydroxyalkanoate, or another biodegradable polymer.

In certain embodiments, the flexible material is THORALON (THORATEC, Pleasanton, Calif.). THORALON is described in U.S. Pat. Nos. 4,675,361 and 6,939,377, both of which are incorporated herein by reference. THORALON is a polyurethane base polymer blended (referred to as BPS-215) with a siloxane containing surface modifying additive (referred to as SMA-300). The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates, pore forming agents or inorganic salts. Preferably the particulate is insoluble in the solvent. Examples of solvents include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can be substantially equal to the diameter of the salt grains.

The porous polymeric sheet can have a void-to-volume ratio from about 0.40 to about 0.90. Preferably the void-to-volume ratio is from about 0.65 to about 0.80. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. No. 6,752,826 and U.S. Publication No. 2003/0149471 A1, published Aug. 7, 2003, both of which are incorporated herein by reference.

Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes may also be employed. These include polyurethane ureas that preferably include a soft segment and include a hard segment formed from a diisocyanate and diamine. For example, polyurethane ureas with soft segments such as polytetramethylene oxide, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

The diisocyanate used as a component of the hard segment may be represented by the formula OCN—R—NCO, where —R— may be aliphatic, aromatic, cycloaliphatic or a mixture of aliphatic and aromatic moieties. Examples of diisocyanates include tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, or mixtures thereof.

Biocompatible polyurethanes modified with cationic, anionic and aliphatic side chains may also be used. See, for example, U.S. Pat. No. 5,017,664.

Other biocompatible polyurethanes include: segmented polyurethanes, such as BIOSPAN; polycarbonate urethanes, such as BIONATE; and polyetherurethanes such as ELAST-HANE; (all available from POLYMER TECHNOLOGY GROUP, Berkeley, Calif.).

Other biocompatible polyurethanes include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10,-20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10,-20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Publication No. 2002/0187288 A1, published Dec. 12, 2002, which is incorporated herein by reference.

In addition, any of these biocompatible polyurethanes may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

In another embodiment of the invention, the flexible material is formed from a polyparaxylene ("parylene") or a parylene derivative, for example parylene C or parylene N.

For example, the parylene or parylene derivative is created by first heating p-xylene or a suitable derivative at an appropriate temperature (for example, at about 950° C.) to produce the cyclic dimer di-p-xylylene (or a derivative thereof). The resultant solid can be separated in pure form, and then cracked and pyrolyzed at an appropriate temperature (for example, at about 680° C.) to produce a monomer vapor of p-xylylene (or derivative); the monomer vapor is cooled to a suitable temperature (for example, below 50° C.) and the flexible body formed by vapor phase deposition.

In other embodiments of the invention, the flexible material is comprised of a naturally derived or synthetic collagenous material, and especially an extracellular matrix material. Suitable extracellular matrix materials ("ECM material") include, for instance, submucosa (including, for example, small intestinal submucosa ("SIS"), stomach submucosa, urinary bladder submucosa, or uterine submucosa), renal capsule membrane, dura mater, pericardium, serosa, and peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present invention, and their isolation and treatment, reference can be made to U.S. Pat. Nos. 4,902,508, 5,554,389, 5,993,844, 6,206,931, and 6,099,567, the contents of which are incorporated by reference. Renal capsule tissue can also be obtained from warm blooded vertebrates, as described more particularly in copending U.S. Publication No. 2003/0014126A1, published Jan. 16, 2003, and International Patent Application Serial No. PCT/US02/20499 filed Jun. 28, 2002, published Jan. 9, 2003 as W003002165, the contents of which are incorporated by reference.

In one embodiment of the invention, the ECM material is porcine SIS. SIS can be prepared according to the method disclosed in U.S. Publication No. 2004/0180042A1, published Sep. 16, 2004, the contents of which are incorporated by reference.

The barbs and hooks of the present invention may also be made with any suitable biocompatible material. These include for example metals such as nitinol or other shape-memory materials, or stainless steel, as well as resorbable or nonresorbable polymeric materials, including those discussed above. Biocompatible adhesives suitable for use in the present invention include, for example, cyanoacrylates, fibrin glues, and hydrophilic-based crosslinking adhesives. Other biocompatible adhesives suitable for use in the present invention are well known to those skilled in the art.

In one embodiment of the invention, the stiffening member is formed from the same material as is the flexible body of the shaped valve cusp. In this embodiment, the stiffening member can be made by folding, rolling, or otherwise gathering and securing material to provide reinforcement of the stiffening member. Alternatively, stiffening member may be formed by molding the stiffening member to have an increased thickness relative to the remainder of the body of the shaped valve cusp. The stiffening member may also be formed by crosslinking the material comprising the stiffening member where the stiffening member is made of collagenous materials.

The stiffening member can also be formed of a material different from that forming the body of the shaped valve cusp. For example, the stiffening member may be formed of a biocompatible metal or metal alloy such as stainless steel, nickel, silver, platinum, gold, titanium, tantalum, iridium, tungsten, Nitinol, inconel, or the like or alloys of any of these, carbon or carbon fiber, cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, a fluoroplastic, such as polytetrafluoroethylene, or another biocompatible polymeric material, or mixtures or copolymers of these, polylactic acid, polyglycolic acid or copolymers thereof, a polyanhydride, polycaprolactone, polyhydroxybutyrate valerate or another biodegradable polymer, or mixtures or copolymers of these, a protein, an extracellular matrix component, collagen, fibrin or another biologic agent; or a suitable mixture of any of these.

Suitable metals or metal alloys include: stainless steels (e.g., 316, 316L or 304), nickel-titanium alloys including shape memory or superelastic types (e.g., nitinol or elastinite); inconel; noble metals including copper, silver, gold, platinum, paladium and iridium; refractory metals including molybdenum, tungsten, tantalum, titanium, rhenium, or niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials, including magnesium; or other biocompatible metals and/or alloys thereof.

In certain embodiments of the present invention, the stiffening member extends continuously from the anchoring element on the base edge and terminates at the pushing surface on the top edge. In other embodiments, the stiffening element consists of one or more elements positioned within the valve body so that a force applied at the pushing surface is transmitted from one element to the next and eventually to the anchoring element. In such embodiments, the total length of the elements of the stiffening member is 99, 95, 90 or 80 percent of the distance between the anchoring element and the pushing surface.

In certain configurations, the stiffening member is formed from a plurality of interconnecting elements, allowing the stiffening member to be folded in a restrained configuration during delivery. After positioning at the site of placement of the frameless grafting prosthesis, the constraint is removed, allowing the elements to lock into an expanded configuration so as to allow a force applied at the pushing surface to be transmitted to the anchoring element. For example, the stiffening member can be composed of a plurality of hollow tubular elements placed around a central flexible spring having its ends attached to the two end elements. The spring is expandable to allow the elements to be folded in a constrained configuration during delivery. However, when the constraint is removed, the spring will contract towards its unexpanded configuration and unfold the elements of the stiffening member. In one embodiment, an end of at least one element to configured to telescope into an immediately adjacent member so as to lock the two members together.

Alternatively, the stiffening member can be formed from a shape-memory or superelastic material. The stiffening member can be restrained in the deformed or folded condition inside a delivery sheath typically to facilitate the insertion into a patient's body. Once positioned within the body lumen, the restraint on the stiffening member can be removed, thereby reducing the stress thereon so that the superelastic support structure returns towards its original undeformed shape through isothermal transformation back to the austenitic phase.

Figure 4:
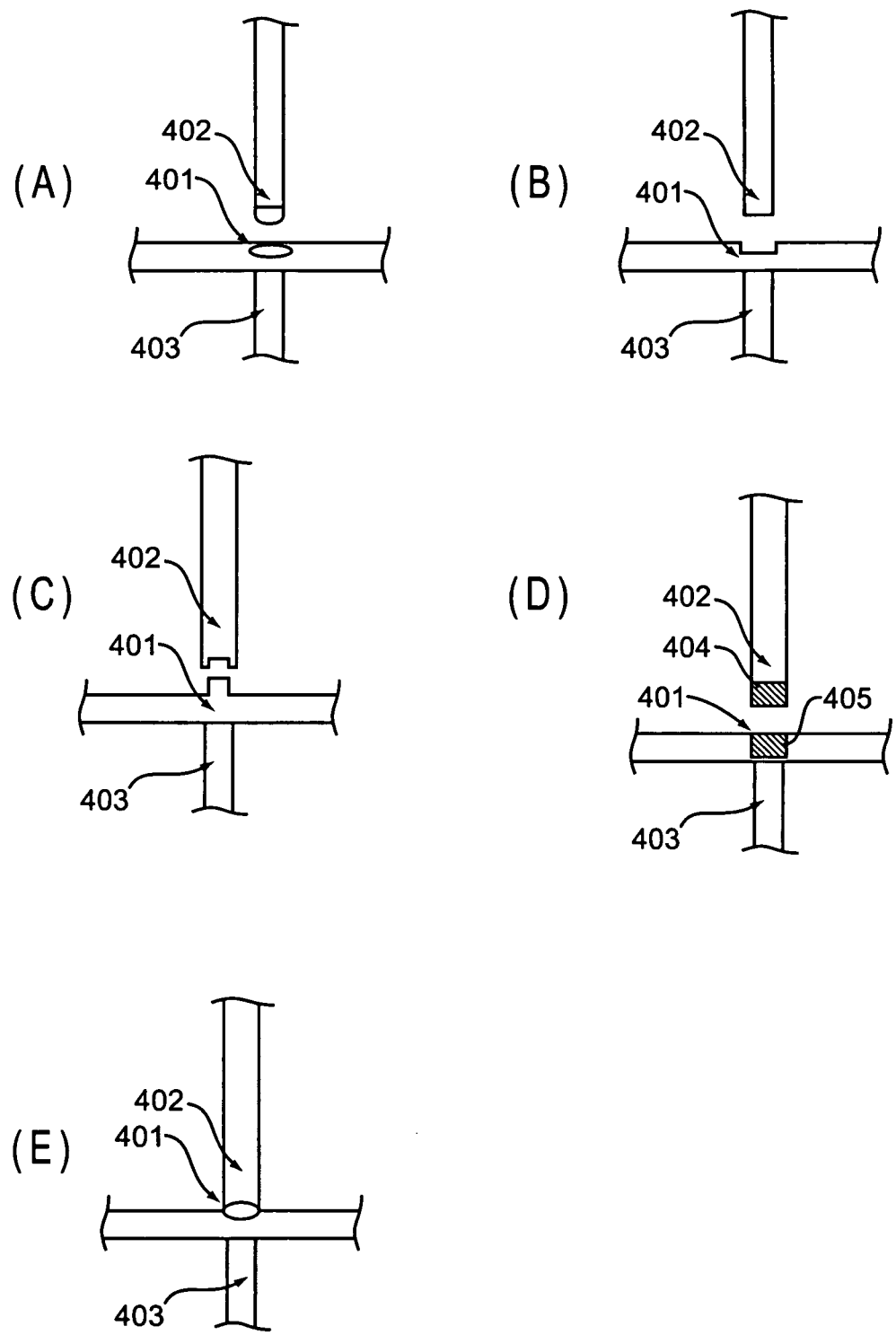
FIGS. 4 (a)-(e) provide schematic views of a pushing surface present on the top edge of a shaped valve cusp.

In one embodiment, the pushing surface is formed on the surface of the top edge of the shaped valve cusp and is defined by the interface of the top edge and the stiffening member, as shown, for example, in FIG. 1 and FIG. 3. With reference now to FIG. 4, shown are illustrative embodiments of the pushing surface 401. FIG. 4(a) shows a pushing surface comprising the end surface of stiffening member 403. Alternatively, as is shown in FIG. 4(b) and FIG. 4(c), the pushing surface may be adapted to provide for an interference fit with pushing rod 402.

In another embodiment the pushing surface and or the pushing rod contain a magnetic or magnetically responsive material, as is illustrated in FIG. 4(d). Here, region 404 of pushing rod 402 and region 405 of pushing surface 401 interact via a magnetic force. Regions 404 and 405 may contain magnets or a magnetically responsive material arranged so that an attractive or a repulsive magnetic force exists between pushing rod 402 and pushing surface 401. Alternatively, one of regions 404 and 405 can contain a magnetic material and the other can contain a magnetically responsive material that becomes magnetized in the presence of a magnetic field.

In yet another embodiment, as illustrated in FIG. 4(e), a biocompatible adhesive 406 is applied to the pushing surface 401. In this embodiment, the biocompatible adhesive 406 is chosen so that a bond exists between the pushing rod and pushing surface during delivery of the frameless grafting prosthesis, and so that this bond can be broken after attachment of the shaped valve cusp to the lumen wall.

In one embodiment, the frameless grafting prosthesis includes a radiopaque marker used to facilitate orientation of the device. Such a radiopaque marker may include, for example, iodine-containing compounds, barium-containing compounds, gold, tantalum, platinum, tungsten or another heavy metal. The radiopaque marker may be present in the stiffening member, the anchoring element, or in another portion of the body of the frameless grafting prosthesis.

Attachment of the Shaped Valve Cusp to the Stiffening Member

Another aspect of the present invention provides methods for attaching a shaped valve cusp to the stiffening member. The valve cusp and stiffening member can be attached by any appropriate attachment means, including but not limited to, adhesive, fasteners, and tissue welding using heat and/or pressure. Alternatively, the valve cusp may be formed around the stiffening member by an appropriate means, including but not limited to vapor deposition, spraying, electrostsatic deposition, ultrasonic deposition, or dipping.

In one embodiment of the invention, the valve cusp is formed from a non-porous biocompatible polyurethane based polymer such as non-porous THORALON. According to one method of attachment, a solution comprising a dissolved THORALON is coated and dried on a mandril to form a valve cusp.

A solution for forming non-porous THORALON can be made by mixing the polyetherurethane urea (BPS-215) and the surface modifying additive (SMA-300) in a solvent, such as dimethyl formamide (DMF), tetrahydrofuran (THF), dimethyacetamide (DMAC), or dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments.

The entire composition can be cast as a sheet, or coated onto an article such as a mandril or a mold. In one example, the composition can be dried to remove the solvent. The mandril can be made from any suitable material that permits the THORALON to coated, dried on and removed from the mandril surface. Suitable materials include stainless steel and glass. In one embodiment, at least a portion of the outer surface of the mandril is formed in the desired shape of a valve cusp. The valve cusp can be formed by coating a thin layer of a solution of THORALON onto the shaped portion of the mandril, drying the coating of the THORALON on the mandril surface, and carefully removing the dried layer of THORALON.

The valve cusp can be attached to the support frame by any suitable technique. In one embodiment, the valve cusp comprises THORALON that is attached to the stiffening member by being formed around and encapsulating portions of the stiffening member. In one method, a solution comprising dissolved THORALON is sprayed and dried on an assembly formed by fitting at least a portion of the stiffening member over a mandril.

In one embodiment, one or more pre-coating layer(s) of THORALON are coated onto at least a portion of the mandril. Next, the stiffening member is fitted onto the mandril. Third, a solution comprising a DMAC solution of non-porous THORALON is coated onto the assembly comprising the mandril and the stiffening member using any suitable method, including spraying or dipping.

In one embodiment, a solution of THORALON is sprayed from a spray gun onto the assembly and the mandril is rotated during spraying process to promote uniform coating of the mandril. Any suitable rate of rotation can be used that provides for a uniform coating of the mandril and retains the coated material on the surface of the mandril. In one embodiment, the mandril is rotated at a rate of about 1 rpm.

When a pre-coating layer is present on the mandril, the THORALON adheres to the pre-coating layer as the solution of THORALON is spray coated onto the surface of the assembly and forms a sheet of THORALON that encapsulates portions of the stiffening member. Optionally, one or more bioactive agents can be coated onto the mandril with the THORALON. In certain embodiments, one or more bioactive agents are incorporated into the stiffening member by, for example, coating onto the surface of the stiffening member, depositing into holes or wells formed in the stiffening member and/or mixing with the material forming the stiffening member.

In one embodiment, the pre-coating layer is first dried on the mandril, then the stiffening member is placed over the coated mandril, and finally second layer of THORALON is spray coated over the support frame as a solution comprising a suitable solvent such as DMAC and THORALON. The solvent in the spray solution preferably partially solubilizes the pre-coating layer so that one fused layer of THORALON is formed. The fused layer can encapsulate portions of the stiffening member and be solidified by evaporation of residual solvent, thereby joining the THORALON to the stiffening member. The residual solvent in the fused layer can be evaporated by heating the valve prosthesis on the mandril.

Alternatively, valve cusp can be attached to the stiffening member by other methods. In one embodiment, the valve cusp is attached to the stiffening member using stitching through the valve cusp material and around a portion of the stiffening member. Adhesives, tissue welding or cross linking may also be used to join the valve cusp material to the stiffening member.

An electrostatic spray deposition (ESD) method of coating the valve cusp material onto a mandril can also be used to form a valve cusp. In this embodiment, particles in the sprayed solution of valve cusp material are electrostatically charged when leaving the nozzle of the spray gun and the mandril is maintained at an electrical potential or grounded to attract the charged particles from the sprayed solution of valve cusp material. The solution of valve cusp material is first dissolved in a solvent and then sprayed onto the mandril using an ESD process.

The ESD process generally depends on the principle that a charged particle is attracted towards a grounded target. Without being confined to any theory, the typical ESD process may be described as follows. The solution that is to be deposited on the mandril is typically charged to several thousand volts (typically negative) and the mandril held at ground potential. The charge of the solution is generally great enough to cause the solution to jump across an air gap of several inches before landing on the target. As the solution is in transit towards the target, it fans out in a conical pattern which aids in a more uniform coating. In addition to the conical spray shape, the charged particles are further attracted towards the conducting portions of the target, rather than towards any non-conductive region of the target, leaving the coating mainly on the conducting regions of the target.

Generally, the ESD method allows for control of the coating composition and surface morphology of the deposited coating. In particular, the morphology of the deposited coating may be controlled by appropriate selection of the ESD parameters, as set forth in WO 03/006180 (Electrostatic Spray Deposition (ESD) of biocompatible coatings on Metallic Substrates), the contents of which are incorporated herein by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The deposition of porous coatings is also possible with the ESD method.

One hypothetical example of an electrostatic spraying apparatus and method is provided. Specifically, a solution of a non-porous THORALON material could be loaded into a 20 mL syringe of an ESD apparatus from Teronics Development Corp., which can then be mounted onto a syringe pump and connected to a tub that carries the solution to a spray head. The syringe pump could then used to purge the air from the solution line and prime the line and spray nozzle with solution. An electrical connection to the nozzle could supply the required voltage. An electrical connection could be provided to hold the mandril at grounding potential.

A motor could then be activated to rotate the mandril at a constant speed of about 1 rpm. The syringe pump could then be activated to supply the nozzle with a consistent flow of solution, and the power supply could be activated to provide a charge to the solution and cause the solution to jump the air gap and land on the mandril surface. As the coated surface is rotated away from the spray path, the volatile portion of the solution could be evaporated leaving a coating of THORALON behind. The mandril could be continually rotated in the spray pattern until the desired amount of non-porous THORALON material accumulates. During the coating process, the mandril could preferably be kept at ambient temperature and humidity, the solution could be pumped at a rate of about 2-4 cm$^3$/hr through the spray gun (which can be placed at a horizontal distance of approximately 6 cm from the mandril), and the bias voltage between the spray nozzle and the mandril should be approximately 10-17 kilovolts.

A stiffening member could then be placed over a mandril (Teronics Development Corp., 2 mm×30 mm) so that at least a portion of the stiffening member makes an electrical connection with the mandril. The mandril could again be continually rotated in the spray pattern until the desired amount of non-porous THORALON material accumulates.

Where it is desired that portions of the perimeter of the valve cusp material are not attached to the stiffening member, the valve cusp material may be cut to free the material from the stiffening member. Alternatively, a mask may be used to cover portions of the stiffening member to prevent attachment of THORALON. The mask can be made from any suitable material that permits the THORALON to coated, dried on and removed from the mask surface. In one embodiment, a mask could be applied to the mandril surface before application of pre-coating layer(s) of THORALON. After the pre-coating layer(s) are applied, the mask could be removed and the support frame placed on the mandril. The mandril could again be continually rotated in the spray pattern until the desired amount of non-porous THORALON material accumulates. Only those portions of the stiffening member placed over portions of the mandril having a pre-coating of THORALON would be enclosed in THORALON.

Further examples of methods of preparation of valve prostheses, including methods of attaching a valve leaflet to a support frame, can be found in U.S. Publication No. 2004/0186558 A1, published Sep. 23, 2004, the contents of which are incorporated by reference.

Incorporation of Bioactive Agents

Frameless grafting prostheses of the present invention can include one or more bioactive agents. Selection of the type of bioactive agent, the portions of the prosthesis comprising the bioactive agent and the manner of attaching the bioactive agent to the valve prosthesis can be chosen to perform a desired therapeutic function upon implantation and, in particular, to achieve controlled release of the bioactive agent.

For example, a bioactive agent can be combined with a biocompatible polyurethane, impregnated in an extracellular collagen matrix material, or coated over any portion of the valve prosthesis. For example, the bioactive agent may be incorporated into the flexible valve body and/or the stiffening member. In one embodiment, a bioactive agent is coated on the surface of the flexible valve body or impregnated in the flexible valve body. In another embodiment, a bioactive material is coated onto or contained within the stiffening member.

A bioactive agent can be incorporated in or applied to portions of the frameless grafting prosthesis by any suitable method that permits controlled release of the bioactive agent material and the effectiveness thereof for an intended purpose upon implantation in the body vessel. The configuration of the bioactive agent on or in the valve prosthesis will depend in part on the desired rate of elution for the bioactive agent. Bioactive agents can be coated directly on the frameless grafting prosthesis or can be adhered to the prosthesis surface by means of a coating. For example, a bioactive agent can be blended with a polymer and spray or dip coated on the prosthesis surface. For example, a bioactive agent material can be posited on the surface of the prosthesis and a porous coating layer can be posited over the bioactive agent material. The bioactive agent material can diffuse through the porous coating layer. Multiple porous coating layers and or pore size can be used to control the rate of diffusion of the bioactive agent material. The coating layer can also be nonporous wherein the rate of diffusion of the bioactive agent material through the coating layer is controlled by the rate of dissolution of the bioactive agent material in the coating layer.

The bioactive agent material can also be dispersed throughout the coating layer, by for example, blending the bioactive agent with the polymer solution that forms the coating layer. If the coating layer is biostable, the bioactive agent can diffuse through the coating layer. If the coating layer is biodegradable, the bioactive agent is released upon erosion of the biodegradable coating layer.

Bioactive agents may be bonded to the coating layer directly via a covalent bond or via a linker molecule which covalently links the bioactive agent and the coating layer. Alternatively, the bioactive agent may be bound to the coating layer by ionic interactions including cationic polymer coatings with anionic functionality on bioactive agent, or alternatively anionic polymer coatings with cationic functionality on the bioactive agent. Hydrophobic interactions may also be used to bind the bioactive agent to a hydrophobic portion of the coating layer. The bioactive agent may be modified to include a hydrophobic moiety such as a carbon based moiety, silicon-carbon based moiety or other such hydrophobic moiety. Alternatively, the hydrogen bonding interactions may be used to bind the bioactive agent to the coating layer.

The bioactive agent can optionally be applied to or incorporated in any suitable portion of the prosthesis. The bioactive agent can be applied to or incorporated in the prosthesis, a polymer coating applied to the prosthesis, a material attached to the prosthesis or a material forming at least a portion of the prosthesis. The bioactive agent can be incorporated within the material forming the stiffening member, or within holes or wells formed in the surface of the stiffening member. The prosthesis can optionally comprise a coating layer containing the bioactive agent, or combinations of multiple coating layers configured to promote a desirable rate of elution of the bioactive from the valve prosthesis upon implantation within the body.

A coating layer comprising a bioactive agent can comprise a bioactive agent and a biostable polymer, a biodegradable polymer or any combination thereof. In one embodiment, the bioactive agent is blended with a biostable polymer to deposit the bioactive agent within the porous channels within the biostable polymer that permit elution of the bioactive agent from the valve prosthesis upon implantation. Alternatively, a blend of the bioactive and the bioabsorbable polymer can be incorporated within a biostable polymer matrix to permit dissolution of the bioabsorbable polymer through channels or pores in the biostable polymer matrix upon implantation in the body, accompanied by elution of the bioactive agent.

Multiple coating layers can be configured to provide a prosthesis with a desirable bioactive agent elution rate upon implantation. The prosthesis can comprise a diffusion layer positioned between a portion of the prosthesis that comprises a bioactive agent and the portion of the prosthesis contacting the body upon implantation. For example, the diffusion layer can be a porous layer positioned on top of a coating layer that comprises a bioactive agent. The diffusion layer can also be a porous layer positioned on top of a bioactive agent coated on or incorporated within a portion of the prosthesis.

A porous diffusion layer is preferably configured to permit diffusion of the bioactive agent from the prosthesis at a desirable elution rate upon implantation within the body. Prior to implantation in the body, the diffusion layer can be substantially free of the bioactive agent. Alternatively, the diffusion layer can comprise a bioactive agent within pores in the diffusion layer. Optionally, the diffusion layer can comprise a mixture of a biodegradable polymer and a bioactive positioned within pores of a biostable polymer of a diffusion layer.

In another embodiment, the porous diffusion layer can comprise a mixture of a biodegradable polymer and a biostable polymer, configured to permit absorption of the biodegradable polymer upon implantation of the prosthesis to form one or more channels in the biostable polymer to permit an underlying bioactive agent to diffuse through the pores formed in the biostable polymer.

More than one bioactive agent may be present in or on the prosthesis. For example one bioactive agent may be contained on one surface of the prosthesis and another bioactive agent contained on another surface. Likewise, one bioactive agent may be contained in or on the stiffening member and another bioactive agent in or on a valve cusp. The present invention also includes embodiments having multiple coating layers where at least two of the coating layers include a bioactive agent.

In one embodiment, the prosthesis is coated with a coating of between about 1 µm and 50 µm, or preferably between 3 µm and 30 µm, although any suitable thickness can be selected. The coating can comprise a bioactive material layer contacting a separate layer comprising a carrier, a bioactive material mixed with one or more carriers, or any combination thereof. The carrier can be biologically or chemically passive or active, but is preferably selected and configured to provide a desired rate of release of the bioactive material. In one embodiment, the carrier is a bioabsorbable material, and one preferred carrier is poly-L-lactic acid. U.S. Publication No. 2004/0034409A1, published on Feb. 19, 2004, describes methods of coating a bioabsorbable metal support frame with bioabsorbable materials such as poly-L-lactic acid that are incorporated herein by reference.

Medical devices comprising an antithrombogenic bioactive material are particularly preferred for implantation in areas of the body that contact blood. An antithrombogenic bioactive material is any bioactive material that inhibits or prevents thrombus formation within a body vessel. The medical device can comprise any suitable antithrombogenic bioactive material. Types of antithrombotic bioactive materials include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive materials inhibit the adhesion, activation, and aggregation of platelets, which are key components of thrombi and play an important role in thrombosis. Fibrinolytic bioactive materials enhance the fibrinolytic cascade or otherwise aid is dissolution of a thrombus.

Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive materials include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive materials such as endothelial progenitor cells or endothelial cells.

Other examples of bioactive coating compounds include antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as (GP) $II_b/III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR α-agonist, a PPAR δ agonist and RXR agonists, as disclosed in published U.S. Publication Number 2004/0073297A1, published Apr. 15, 2004 and incorporated in its entirety herein by reference.

Delivery Systems and Methods of Delivery

The present invention also provides for delivery systems and methods of delivery of the frameless grafting prosthesis. The frameless grafting prosthesis as described herein can be delivered to any suitable body vessel, including a vein, artery, biliary duct, ureteral vessel, body passage or portion of the alimentary canal. Methods for delivering a frameless grafting prosthesis as described herein to any suitable body vessel are also provided, such as a vein, artery, biliary duct, ureteral vessel, body passage or portion of the alimentary canal. While many preferred embodiments discussed herein discuss implantation of a frameless grafting prosthesis in a vein, other embodiments provide for implantation within other body vessels. In another matter of terminology there are many types of body canals, blood vessels, ducts, tubes and other body passages, and the term "vessel" is meant to include all such passages.

In certain configurations, a rapid exchange valve prosthesis delivery balloon catheter allows exchange from a balloon angioplasty catheter to a prosthesis delivery catheter without the need to replace the angioplasty catheter guide wire with an exchange-length wire guide before exchanging the catheters. Such delivery methods are described in U.S. Pat. Nos. 5,690,642, 5,814,061 and 6,371,961, the contents of which are incorporated by reference.

Figure 5:
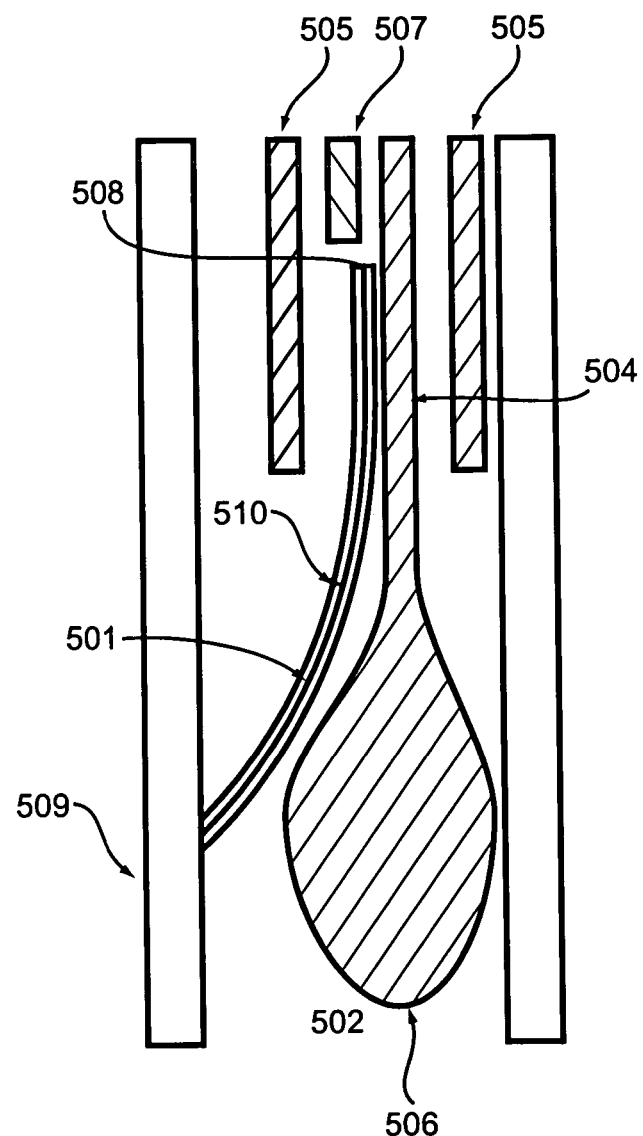
FIG. 5 provides a schematic view of a delivery system for a frameless grafting prosthesis.

FIG. 5 illustrates one method of delivering the frameless grafting prosthesis having one shaped valve cusp 501 to a site within a body lumen 502 using a deployment device. The deployment device is generally adapted for delivery through the vessel lumen, and includes a long, flexible body having a central portion 504 and a retractable sheath 505 surrounding the central portion 504. An enclosure is formed between the central portion 504 and the retractable sheath 505. During delivery, the frameless grafting prosthesis 501 is contained within the enclosure, as is illustrated in FIG. 5.

Push rod 507 is positioned inside the enclosure and adjacent to or in contact with the pushing surface 508 of frameless grafting prosthesis 501. Upon delivery to the placement site, retractable sheath 505 is retracted to form an opening at the end of the enclosure. Push rod 507 is contacted with pushing surface 508 and employed to push frameless grafting prosthesis 501 from the opening. Force applied to pushing surface 508 is transmitted to anchoring element 509 via stiffening member 510. The transmitted force is sufficient to push anchoring element 509 against, into or through lumen wall 502 to attach frameless grafting prosthesis 501 to lumen wall 502.

After attachment of frameless grafting prosthesis 501 to lumen wall 502, central region 504 of the deployment device is withdrawn. In one embodiment, central portion 505 contains an expanded end region 506. In this embodiment, expanded end region 506 contacts the base and side edges of frameless grafting prosthesis 501 as it is withdrawn and pushes any additional anchoring elements present on these edges against, into or through lumen wall 502 to further attach frameless grafting prosthesis 501 to lumen wall 502.

In an alternative embodiment, end region 506 contains an expendable frame or balloon. In this embodiment, end region 506 is not expanded during the initial attachment of frameless grafting prosthesis 501 to lumen wall 502 by push rod 507. After attachment of anchoring element 509, end region 506 is expanded to push any additional anchoring elements present on the base and side edges of frameless grafting prosthesis 501 against, into or through lumen wall 502 to further attach frameless grafting prosthesis 501 to lumen wall 502.

The present invention also provides for delivery systems and methods of delivery of the frameless grafting prosthesis having more than one shaped valve cusp, for example, for the delivery of the frameless grafting prosthesis having two shape valve cusps. Such a frameless grafting prosthesis as shown in FIG. 3.

For the delivery of a bicuspid valve, such a deployment system can include an additional enclosure to accommodate a second shaped valve cusp and a second push rod to push the second shaped valve cusp. Alternatively, the pushing surfaces of both shaped valve cusps may be positioned adjacent to or in contact with separate regions of the end of the push rod.

Controlled Retrograde Flow

The frameless grafting prosthesis can be configured to permit a controlled amount of retrograde flow through a body vessel despite the presence of the frameless grafting prosthesis. This may be desirable for a variety of reasons. For example, allowance of a controlled amount of retrograde flow can prevent pooling of fluid when the frameless grafting prosthesis is in a closed or substantially closed configuration in the body vessel.

Figure 6:
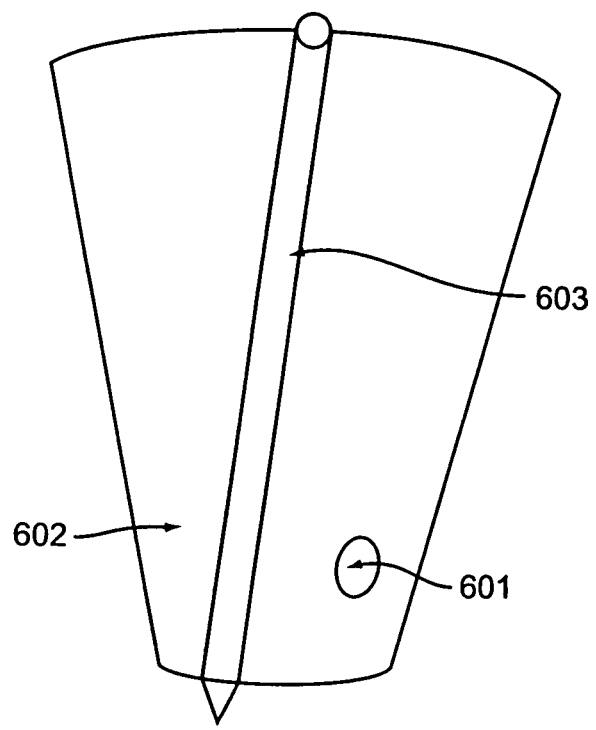
FIG. 6 provides a perspective view of a frameless grafting prosthesis having an aperture to allow limited retrograde flow.

Any suitable means for permitting a controlled amount of retrograde flow to pass through the frameless grafting prosthesis can be used in any of the embodiments described herein. FIG. 6 illustrates an exemplary embodiment of a frameless grafting prosthesis that includes a suitable means for permitting a controlled amount of retrograde flow. In this embodiment, the frameless grafting prosthesis includes an aperture 601 through which retrograde flow can pass.

The quantity of retrograde flow that passes through the aperture 601 is controlled by the overall dimensions and configuration of the aperture 601. A larger opening allows a greater amount of retrograde flow to pass through the frameless grafting prosthesis while a relatively smaller opening will allow a relatively lesser amount of retrograde flow to pass. The dimensions and configuration of the aperture 601 of each embodiment can be optimized based upon the vessel in which the frameless grafting prosthesis is placed. The size and configuration selected will depend on several factors, including the vessel size, typical flow volumes and rates, and others. The opening is advantageously sized to allow a desired amount of retrograde flow pass through the opening during periods of retrograde flow. The aperture 601 should be small enough, though, to still allow the frameless grafting prosthesis to substantially prevent retrograde flow when the frameless grafting prosthesis is in a closed configuration.

Thus, the aperture 601 is advantageously sized so as to not allow a majority of retrograde flow to pass through the aperture 601. In one embodiment, the total open area of the aperture 601 is, at a maximum, less than the cross-sectional area of the vessel lumen. As used herein, the term "total open area", in relation to the aperture 601, refers to the total area of the aperture 601 when the entire perimeter of the aperture 601 lies in the same plane.

The aperture 601 advantageously can be sized to mimic the degree of retrograde flow—the leakiness—that is present in a natural valve located at the point of treatment in the body vessel. Accordingly, the dimensions of the aperture 601 can be determined and optimized based upon the vessel in which the frameless grafting prosthesis is to be placed. For venous valve applications, the total open area of the aperture 601 is advantageously less than about 50% of the cross-sectional area of the vessel at the intended point of deployment. More advantageously, the total open area of the aperture 601 is less than about 25% of the total cross-sectional area of the vessel at the intended point of deployment. In one example, a device is configured for placement in a vessel having a total cross-sectional area of about 50 mm$^2$. In this example, the aperture 601 has a total open area of about 20 mm$^2$. Also for venous valve applications, a circular opening with a diameter of between about 0.5 and about 3.0 mm has been found to be suitable. In a specific venous valve example, a circular opening with a diameter of about 1 mm has been found to be suitable. In another specific venous valve example, a circular opening with a diameter of about 2 mm has been found to be suitable.

The aperture 601 can have any suitable shape. Examples of specifically contemplated shapes include circular, ovoid, triangular, square, rectangular, and tear-drop shaped openings. The size chosen for the opening may depend on the shape of the opening and/or the orientation of the opening relation to the direction of fluid flow. Furthermore, multiple openings can be used. In these embodiments, the sum total open area of all openings is advantageously in accordance with the parameters described above.

The aperture 601 can be positioned the valve body 602 or in the stiffening member 603. If the opening is positioned the stiffening member 603, the dimensions of the aperture 601 are such that the integrity of stiffening member 603 is not compromised.

Medical Products

The present invention also provides packaged, sterile medical products. Such products comprise a frameless grafting prosthesis as described herein contained in sterile packaging. The sterile packaging can contain a single frameless grafting prosthesis, or a plurality of frameless grafting prostheses. Medical products comprising a frameless grafting prosthesis combined with a deployment device are also provided.

When more than one frameless grafting prosthesis is included in the sterile packaging, the prostheses can each be of substantially the same size and shape, or, alternatively, can vary with respect to size and shape. In addition, the sterile packaging can have visible indicia identifying the contained prosthesis as, for example, a venous or other vascular valve, and/or can contain or otherwise be associated with printed materials identifying the prosthesis as a venous or other vascular valve and including information concerning its use as a venous or other vascular valve. The sterile packaging can also include visible indicia relating to the dimension of the frameless grafting prosthesis which it contains, and/or relating to the vessel diameter(s) for which the prosthesis is configured.

Each frameless grafting prosthesis of the invention can be constructed so as to have dimensions suited for implantation within a vessel of a given diameter. Also provided within the present invention is a medical valve product line comprising a plurality of packaged, sterile medical products as described above, wherein the plurality of medical products includes packaged prosthesis devices of varying dimensions to suit varying patients or applications, for example the product line including at least 3 differently dimensioned products, e.g. from about 3 to about 20 differently dimensioned products.

The frameless grafting prosthesis can be contained in a sterile packaging in any suitable state. Suitable states include, for example, a hydrated or dehydrated state. A frameless grafting prosthesis can be dehydrated by any means known in the art (e.g., lyophilization or air dried).

While the invention has been illustrated and described in detail in the drawings and foregoing description, the same is to be considered as illustrative and not restrictive in character, it being understood that only exemplary embodiments have been shown and described and do not limit the scope of the invention in any manner. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

What is claimed is:

1. A frameless grafting prosthesis for implantation in a body lumen having a lumen wall, the frameless grafting prosthesis comprising at least one shaped valve cusp comprising:
   a valve body having a top edge, a base edge, and side edges extending from the base edge to the top edge,
   at least one anchoring element attached to the base edge, and
   a stiffening member positioned within the valve body and having first and second ends, the first end directly contacting the anchoring element and the second end comprising a pushing surface, the stiffening member extending from the anchoring element to the top edge of the valve body,
   wherein the stiffening member is less flexible than the valve body and is adapted to allow a force sufficient to attach the anchoring element to the lumen wall to be transmitted from the pushing surface to the anchoring element.

2. The frameless grafting prosthesis of claim 1, wherein the anchoring element is configured to attach to or partially or fully penetrate the lumen wall.

3. The frameless grafting prosthesis of claim 1, wherein the anchoring element is selected from a group consisting of a barb, a hook, and an adhesive.

4. The frameless grafting prosthesis of claim 1, wherein the shaped valve cusp is deformable around an axis generally parallel to the stiffening member.

5. The frameless grafting prosthesis of claim 4, wherein the stiffening element has a thickness greater than a deformable portion of the valve body.

6. The frameless grafting prosthesis of claim 1, wherein the shaped valve cusp is deformable between a first position allowing fluid flow in a first, antegrade, direction and a second position restricting flow in a second, retrograde, direction in response to a change in a direction of fluid flow in the body lumen.

7. The frameless grafting prosthesis of claim 1, further comprising an adhesive applied to the pushing surface.

8. The frameless grafting prosthesis of claim 1, wherein the pushing surface is adapted to receive an end of a push rod.

9. The frameless grafting prosthesis of claim 1, wherein the pushing surface further comprises a magnetic or magnetically responsive element.

10. The frameless grafting prosthesis of claim 1, wherein the shaped valve cusp comprises a polymer.

11. The frameless grafting prosthesis of claim 1, wherein the shaped valve cusp comprises a material selected from the group consisting of a synthetic biocompatible polymer, cellulose acetate, cellulose nitrate, silicone, polyethylene, teraphthalate, polyurethane, polyamide, polyester, polyorthoester, polyanhydride, polyether sulfone, polycarbonate, polypropylene, high molecular weight polyethylene, a fluoroplastic material, polytetrafluoroethylene polylactic acid, polyglycolic acid, a polyanhydride, polycaprolactone, polyhydroxy-butyrate valerate, polyhydroxyalkanoate, a biodegradable polymer, a collagenous material, and mixtures or copolymers thereof.

12. The frameless grafting prosthesis of claim 1, wherein the shaped valve cusp comprises an extracellular matrix.

13. The frameless grafting prosthesis of claim 1, wherein the valve cusp comprises a polyetherurethane urea and a surface modifying additive.

14. The frameless grafting prosthesis of claim 1, wherein the stiffening member comprises a material selected from a group consisting of stainless steel, tantalum, titanium, nitinol, gold, platinum, inconel, iridium, silver, tungsten, a biocompatible metal, and alloys of any of these; carbon, carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, a fluoroplastic material, polytetrafluoroethylene, a biocompatible polymeric material, and mixtures or copolymers of these; polylactic acid, polyglycolic acid and copolymers thereof, a polyanhydride, polycaprolactone, polyhydroxybutyrate valerate or another biodegradable polymer, and mixtures or copolymers of these; a protein, an extracellular matrix component, collagen, fibrin, a biologic agent; and a suitable mixture of any of these.

15. The frameless grafting prosthesis of claim 1, wherein the shaped valve cusp comprises a bioactive agent.

16. The frameless grafting prosthesis of claim 1, wherein the shaped valve cusp further comprises an aperture, wherein the aperture allows limited retrograde flow in the body lumen.

17. The frameless grafting prosthesis of claim 1, wherein the pushing surface extends axially beyond the top edge of the valve body.

18. The frameless grafting prosthesis of claim 17, wherein the anchoring element is continuously formed with the stiffening member.

19. The frameless grafting prosthesis of claim 1, wherein the stiffening member terminates at the second end such that the pushing surface is flush with the top edge of the valve body.

20. The frameless grafting prosthesis of claim 1, wherein the anchoring element is continuously formed with the stiffening member.

* * * * *